United States Patent
Smits

[11] Patent Number: 6,006,122
[45] Date of Patent: Dec. 21, 1999

[54] MEDICAL ELECTRICAL LEAD

[75] Inventor: Karel F. A. Smits, Munstergeleen, Netherlands

[73] Assignee: Medtronic, Inc., Minneapolis, Minn.

[21] Appl. No.: 08/937,510

[22] Filed: Sep. 25, 1997

[51] Int. Cl.$^6$ ..................................................... A61N 1/04
[52] U.S. Cl. ...................... 600/373; 600/375; 600/381; 607/122; 607/126
[58] Field of Search ...................... 607/116, 119, 607/122, 126–132, 101; 606/41; 600/372–381, 11

[56] References Cited

U.S. PATENT DOCUMENTS

| | | | |
|---|---|---|---|
| 3,943,936 | 3/1976 | Rasor et al. | 607/126 |
| 4,317,459 | 3/1982 | Gilman | 128/785 |
| 4,351,345 | 9/1982 | Carney | 607/122 |
| 5,207,226 | 5/1993 | Bailin et al. | 128/661.08 |
| 5,387,233 | 2/1995 | Alferness et al. | 607/126 |
| 5,411,546 | 5/1995 | Bowald et al. | 607/126 |
| 5,423,772 | 6/1995 | Lurie | 604/282 |

OTHER PUBLICATIONS

NASPE Abstracts—Pacing and Clinical Electrophysiology, Apr. 1995, vol. 18, No. 4, Part II "Experience with a New Coronary Sinus Lead Specifically Designed for Permanent Left Atrial Pacing"—C. Daubert et al.

*Primary Examiner*—Michael Peffley
*Assistant Examiner*—David M. Ruddy
*Attorney, Agent, or Firm*—Thomas F. Woods; Harold Patton; Michael J. Jaro

[57] ABSTRACT

A transvenous lead specifically designed for coronary sinus implantation. The lead features a fixation ring positioned adjacent to the electrode. The ring is constructed so as to be readily pliable and bent. The ring functions to wedge or fix the lead within the coronary sinus in such a manner that the electrode is pushed against the vessel wall while the flow of blood through the vessel is not impeded. In alternative embodiments the electrode is positioned on the ring itself. In further alternative embodiments the distal portion of the lead features a pre bent nose to assist in the positioning of the lead into the coronary sinus. The nose may be oriented relative to the ring in any acceptable manner to permit the ring and the electrode to be properly positioned relative to anywhere along the coronary sinus wall.

23 Claims, 4 Drawing Sheets

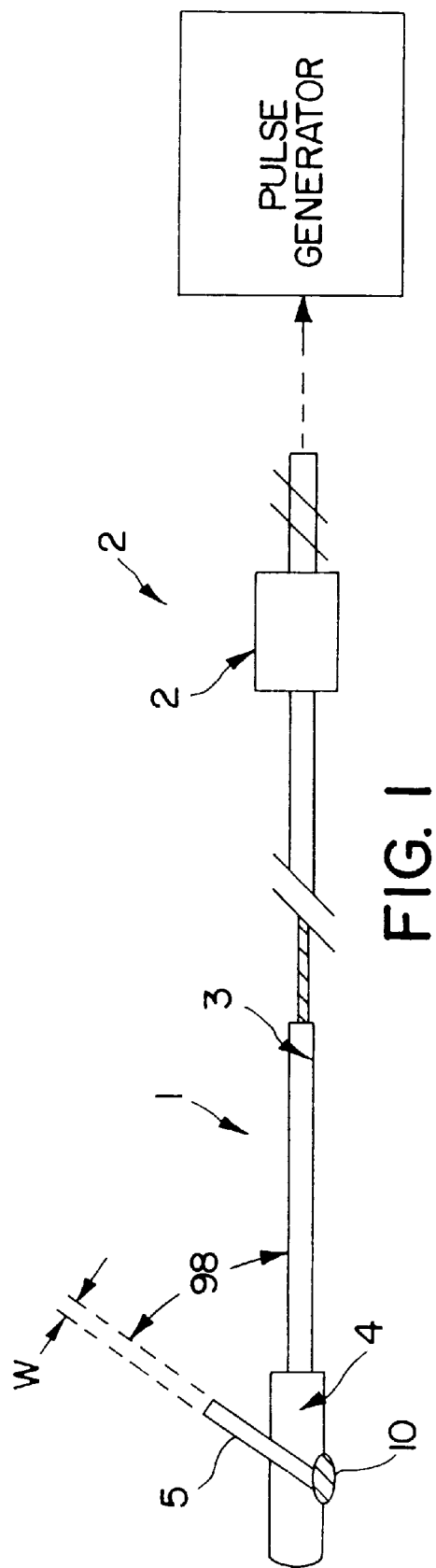
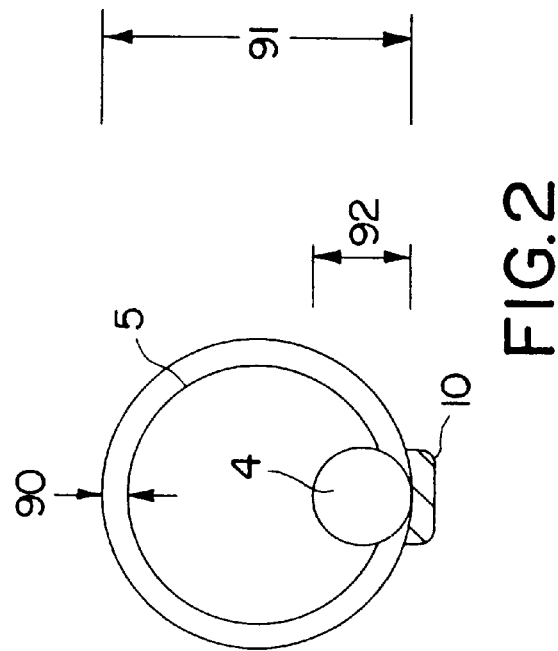

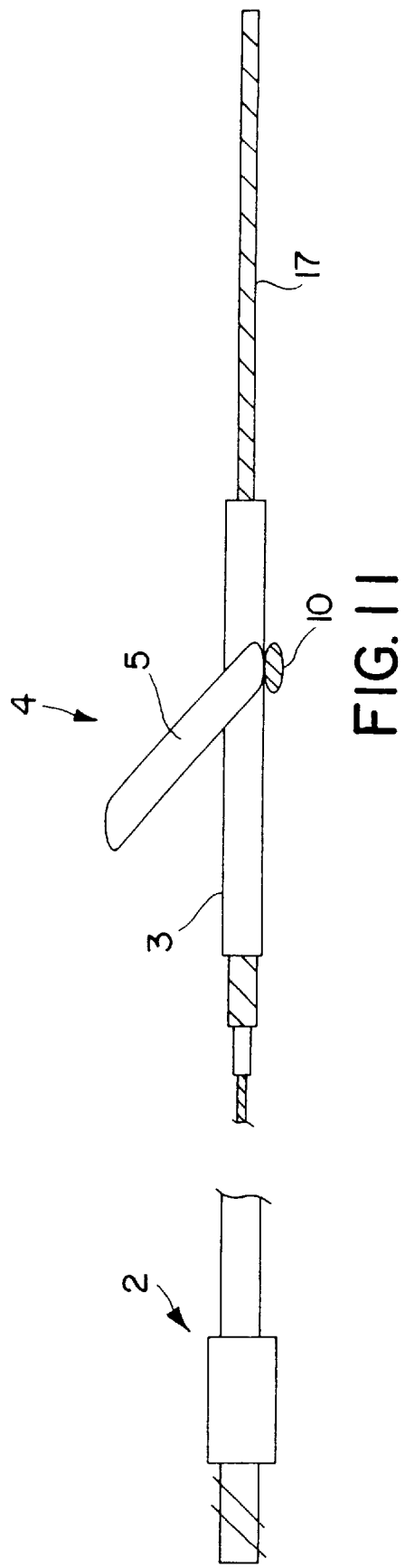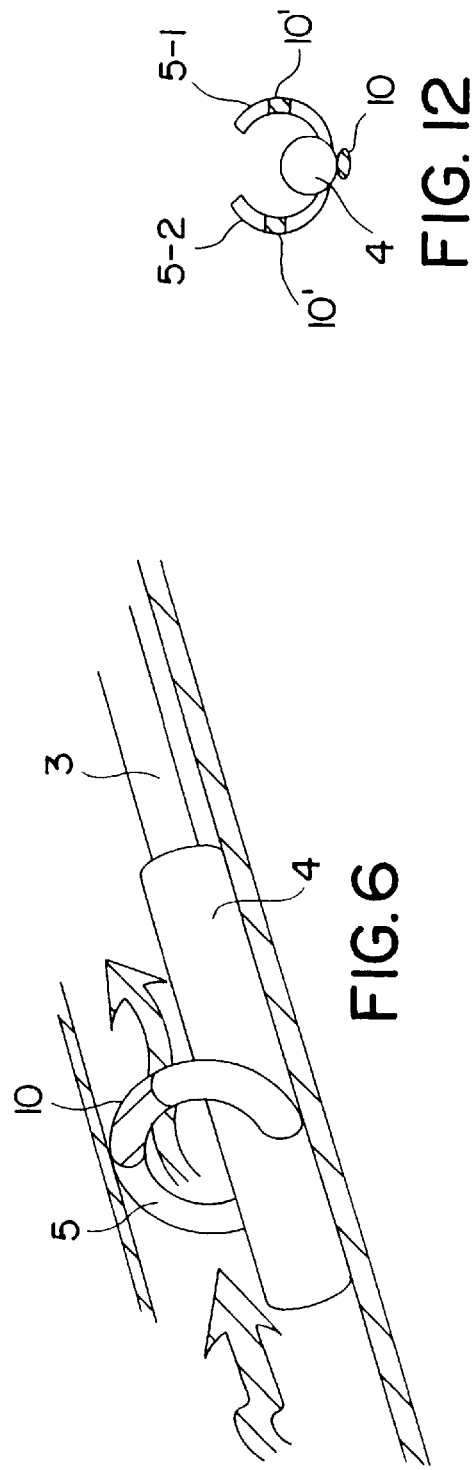

MEDICAL ELECTRICAL LEAD

FIELD OF THE INVENTION

This invention relates to the field of body implantable medical device systems, and in particular to a body implantable medical device system which includes a medical electrical lead particularly designed for implantation into the coronary sinus.

BACKGROUND OF THE INVENTION

Modern electrical therapeutic and diagnostic devices for the heart, such as pacemakers, cardiovertors, and defibrillators, for example, require a reliable electrical connection between the device and a region of the heart. Typically, a medical electrical "lead" is used for the desired electrical connection.

One type of commonly used implantable lead is a transvenous lead. Transvenous leads are positioned through the venous system to attach or electrically connect at their distal end to the heart. At their proximal end, they are connected to typically an implantable pulse generator. Such leads normally took the form of a long, generally straight, flexible, insulated conductor. Among the many advantages of a transvenous lead is that it permits an electrical contact with the heart without physically exposing the heart itself, i.e., major thoracic surgery is not required.

The specific design of a transvenous lead used is often varied depending upon the region of the heart to which it is to be connected. For example, U.S. Pat. No. 4,402,330 of Lindemans discloses a body implantable lead in which the lead body has a J-curve and the distal electrode has a permanent bend. In such a manner, the lead is configured to electrically connect to the right atrium.

While such a lead has been found acceptable for electrically connecting and thus pacing the right atrium, the need exists for a transvenous medical electrical lead which may provide an electrical connection to the left atrium. Of course the left atrium cannot, at present, be transvenously accessed with a lead for chronic implantation due to the direction of blood flow and the present limitations of materials. To be precise, blood flows through the right side of the heart (atrium and ventricle), through the lungs, through the left side of the heart (atrium and ventricle) and then through the rest of the body, including the brain, before returning again to the right side of the heart. Implanted objects, however, often cause minor blood clots and thrombus to form in the blood. These may, on occasion, dislodge and be released into the bloodstream. Because the blood circulates directly from the left atrium and ventricle to the brain, any clots, however minor, could have serious consequences if they were to reach the brain, e.g. a stroke. In contrast, any clots released from an object implanted in the right side of the heart would simply travel to the lungs, where they would lodge without any serious risk. Thus at present, chronic transvenous leads may not be safely implanted within the left side of the heart.

In spite of the difficulties, there remains a great need to be able to electrically stimulate or sense or both the left side of the heart. The most obvious reason is the left side of the heart accounts for the majority of the heart's hemodynamic output. For example, the left ventricle has a greater wall thickness (10–20 mm as compared to 1–5 mm) than the right side. This, of course, is reasonable given that the left side of the heart must pump blood throughout the body while the right side only pumps blood through the lungs.

Because the left side is relatively more important for hemodynamic output, not surprisingly various pathologies may be better treated through stimulation on the left side of the heart. For example, in patients with dilated cardiomyopathy, electrical stimulation of both the right side and the left side of the heart has been shown to be of major importance to improve the patient's well-being and manage heart failure. See, for example, Cazeau et al., "Four Chamber Pacing in Dilated Cardiomyopathy," PACE, Nov. 1994, pgs. 1974–79. See also Brecker and Fontainem, St. et al., "Effects Of Dual Chamber Pacing With Short Atrioventricular Delay In Dilated Cardiomyopathy," Lancet Nov. 1992 Vol. 340 p1308–1312; Xiao H.B. et al., "Effect Of Left Bundle Branch Block On Diastolic Function In Dilated Cardiomyopathy," Br. Heart J 1991, 66(6) p 443–447; and Fontaine G et al, "Electrophysiology Of Pseudofunction," CI.Meere (ed.) Cardiac pacing, state of the art 1979, Pacesymp, 1979 Montreal.

At present there are several techniques for implanting a lead onto or into the left side of the heart. First, of course, is through general thoracic surgery; either via a median sternotomy; intercostal approach; or, in a more limited procedure, a sub-xiphoid approach. These procedures, however, involve major surgery which may be painful and dangerous for the patient, as well as extremely costly. The sub-xiphoid approach, moreover, only permits limited access to the anterolateral surface of the left ventricle as well as to the left atrium. Another approach used is to electrically access the left atrium is through the coronary sinus.

The coronary sinus, however, presents challenges in both implanting the lead in the proper position as well as ensuring the lead maintains sufficient electrical contact with the desired tissue. U.S. Pat. No. 5,423,772 of Lurie et al. discloses a coronary sinus catheter having three sections. Each section has varying degrees of flexibility, with the proximal reinforced section being stiffer than an intermediate section, the intermediate section being stiffer than the softened tip section. The catheter also is curved, with the curve beginning in the intermediate section, the curve further continuing into the softened tip section, where the radius of curvature decreases, i.e., the catheter becomes more curved closer to the tip. One drawback to such a design, however, is that the particular shape of the curve is not ideally suited for electrically accessing the left atrium. In addition, such a catheter is relatively complicated to manufacture due to the required reinforcing braid or other mends in the proximal reinforced section. Finally, such a catheter does not permit introduction of a stylet to assist in the placement of the catheter into the coronary sinus.

It is thus an object of the present invention to provide a medical electrical lead which is suitably shaped to provide an electrical connection through the coronary sinus to one or both of the left chambers of the heart.

A still further object of the present invention is to provide a medical electrical lead having an electrode positioned so that when the lead is implanted into the coronary sinus the electrode is positioned against the coronary sinus wall.

A still further object of the present invention is to provide a medical electrical lead having an electrode which may be positioned along a selected portion of the coronary sinus wall, such as the lower portion of the coronary sinus wall and thus be able to electrically communicate with the left ventricle, or the upper portion of the coronary sinus wall and thus be able to electrically communicate with the left atrium.

A still further object of the present invention is to provide a medical electrical lead having an electrode which may be positioned along a selected portion of the coronary sinus wall but which will minimize the diminishment of any blood flow through the coronary sinus.

SUMMARY OF THE INVENTION

These and other objects are accomplished through the present invention. In one embodiment, the present invention comprises a transvenous lead specifically designed for coronary sinus implantation. The lead of the present invention features a fixation ring positioned adjacent to the electrode. The ring is constructed so as to be readily pliable and bent. The ring functions to wedge or fix the lead within the coronary sinus in such a manner that the electrode is pushed against the vessel wall. Because the ring has a central lumen, however, the flow of blood through the vessel is not impeded. In alternative embodiments the electrode is positioned on the ring itself. In further alternative embodiments the distal portion of the lead features a pre bent nose to assist in the positioning of the lead into the coronary sinus. The nose may be oriented relative to the ring in any acceptable manner to permit the ring and the electrode to be properly positioned relative to anywhere along the coronary sinus wall.

BRIEF DESCRIPTION OF THE FIGS.

FIG. 1 is a side view of a lead according to the present invention.

FIG. 2 is an end view of the lead shown in FIG. 1

FIG. 6 depicts an alternative embodiment of the present invention.

Figure 7A:
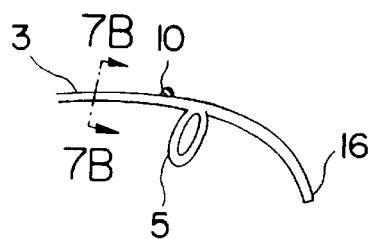
Figure 7B:
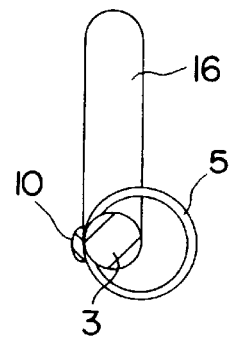

FIGS. 7A & B depict an alternative embodiment of the present invention.

FIGS. 8 A & B depict an alternative embodiment of the present invention.

FIGS. 9 A & B depict an alternative embodiment of the present invention.

FIGS. 10 A & B depict an alternative embodiment of the present invention.

FIG. 11 depicts an alternative embodiment of the present invention.

FIG. 12 depicts an alternative embodiment of the present invention. It should be understood the drawings are not necessarily to scale.

DETAILED DESCRIPTION OF THE INVENTION

FIG. 1 is a perspective view of a lead according to the present invention. As seen, lead 1 essentially has two portions: a connector portion 2 and a lead body portion 3. Distal end of lead body portion features an electrode/anchoring section 4. Connector portion is a standard pacing connector, such as an IS-1 or an IS BI-2, and is used to couple the lead to a pulse generator, as shown. Of course, other connector designs may be used. Lead body portion 3 is preferably constructed using an insulative sheath of a biocompatible polymer, such as silicone, and a coiled conductor of a biocompatible material, such as MP35N. Of course other materials and structures may also be used for each of these components, such as a bundled stranded wire conductor, and still be within the scope of the present invention. Lead body portion couples connector portion 2 to electrode/anchoring section 4. The lead body may additionally feature pacing, sensing or defibrillation electrode. As seen, electrode/anchoring section features a fixation ring 5 disposed on first side of the lead and an electrode 10 disposed on the opposite side of the lead. In the preferred embodiment fixation ring is disposed at an oblique angle 98 relative to the axis of the lead body. In the embodiment shown ring 5 is angled 60 degrees relative to the axis of lead body and in the proximal direction, although any angle between approximately 90 and 30 degrees may be selected. This angling of the ring is an important feature of the present invention because it assists in maintaining the lead in position once properly placed. That is, ring acts like a type of barb to thereby resist proximal movement of the lead. Electrode 10 is constructed using spherical platinum porous powder which has further a platinum black electroplate thereon as is well known in the pacing art. In addition, electrode may further be constructed having a cavity into which is disposed a monolithic controlled release device therein to elute or dispense a drug, such as the sodium salt of dexamethasone, from the electrode into the surrounding tissues, as is well known in the pacing art. In an alternative, the electrode may be treated with a very slightly soluble in water steroid, such as beclomethasone dipropionate anhydrous. Preferably the steroid is applied to the surface of the electrode which contacts tissue when implanted. Further details of such a coating process may be found in U.S. Patent Application of Williams "Medical Electrical Lead" Ser. No. 08/605,591, incorporated herein by reference.

FIG. 2 is an end view of the lead shown in FIG. 1 and best shows the orientation of the fixation ring 5 and electrode 10. As seen ring 5 extends from a first side of electrode/anchoring section 4 to the opposite side. Ring is positioned so as to be tangent to the outer surface of the electrode/anchoring section. Electrode/anchoring section 4 preferably is constructed of silicone, and ring is also preferably constructed of silicone. Ring may have a thickness 90 of anywhere between approximately 0.5–3 millimeters, with 1 millimeter preferred, a width W (depicted in FIG. 1) anywhere between approximately 0.5–4 millimeters, with 2 millimeters preferred, and an outer diameter 91 of anywhere between approximately 6–8 millimeters. Electrode/anchoring section may have an outer diameter 92 of anywhere between approximately 1–3 millimeters, with 2 millimeters preferred. Such small dimensions of the present invention are critical to the effective operation of the lead due to the small sizes of the cardiac veins. For example, a typical coronary sinus is 10 millimeters at its largest diameter (near the outflow to the right atrium) and narrows until it has a diameter of between approximately 2–3 millimeters and merges to the great cardiac vein. Thus any leads having larger sizes could be expected to detrimentally diminish if not completely occlude the flow of blood through the coronary sinus. The coronary sinus vein has a typical length of between 4–6 centimeters. Finally, the fixation of a lead within the coronary sinus is complicated by the fact that, unlike a heart chamber where the fibrotic tissue response is used to assist lead fixation, no such fibrotic response can be expected in the vein. As such no fibrotic tissue response is available to assist in lead fixation.

Figure 3:
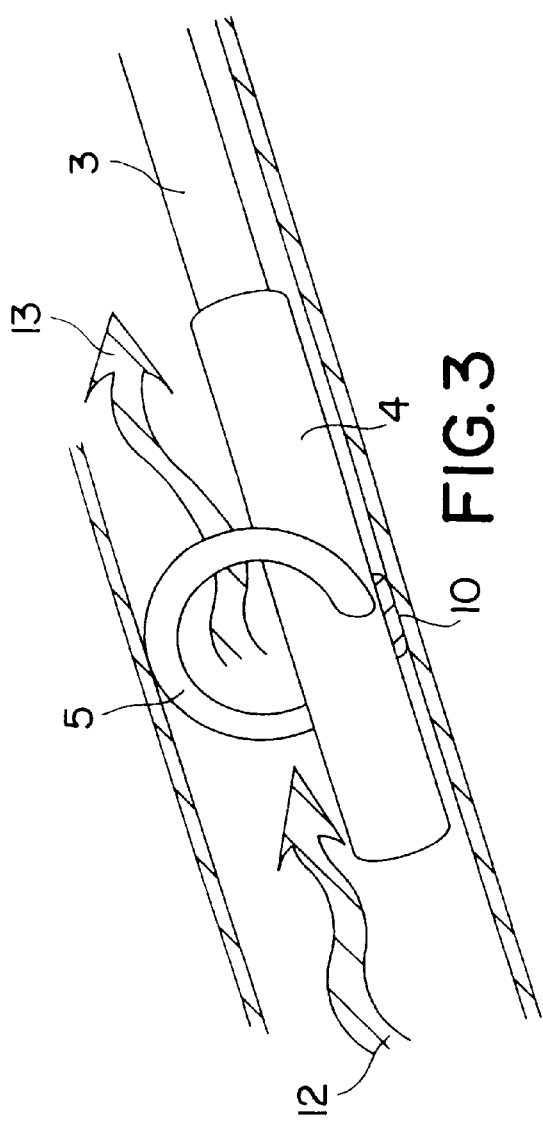
FIG. 3 depicts the distal end of the lead shown in FIG. 1 implanted in the coronary sinus and details the operation of the fixation ring.

FIG. 3 depicts the distal end of the lead shown in FIG. 1 implanted in the coronary sinus and details the operation of the fixation ring. As seen ring is sized to wedge the electrode anchoring portion against the opposite side of the coronary sinus wall. Moreover, the lumen through ring permits blood to flow unimpeded, as depicted by arrows 12, 13. In addition, as already discussed above, the ring and electrode/anchoring section are oriented in a tangential manner so as to maximize the lumen through the ring and minimize the likelihood that there will be any other passageways for blood to flow through once the lead is implanted into the blood vessel. As can be appreciated, shunted and interrupted blood flow can possibly lead to the formation of thrombosis to form, which may hinder blood flow to the point that stagnation occurs in the vessel. The health of the surrounding tissue would be impacted.

Figure 4:
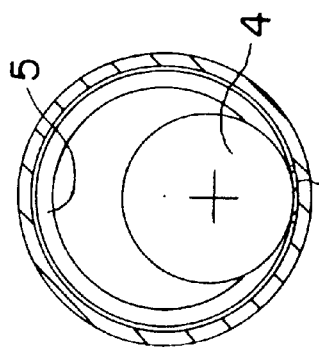
FIG. 4 is an end view of the lead shown in FIG. 3.

FIG. 4 is an end view of the lead shown in FIG. 3. As best seen in this view ring 5 is designed to contact and deform against the vessel wall and thereby elasticity bias the electrode/anchoring section 4 and electrode 10 carried thereon against the vessel wall. in addition, the relatively large lumen through ring permits blood to flow there through unimpeded. As discussed above in regards to FIG. 2, ring is positioned so as to be tangent to the outer surface of the electrode/anchoring section. This is important in that it defines only a single passageway through the vein once the ring is fitted snugly against the vessel wall, that is the passageway defined through the ring itself. This ensures the largest possible passageway is available for the blood to flow through, minimizing any possible pooling or stagnation of the blood which may lead to thrombus forming.

Figure 5:
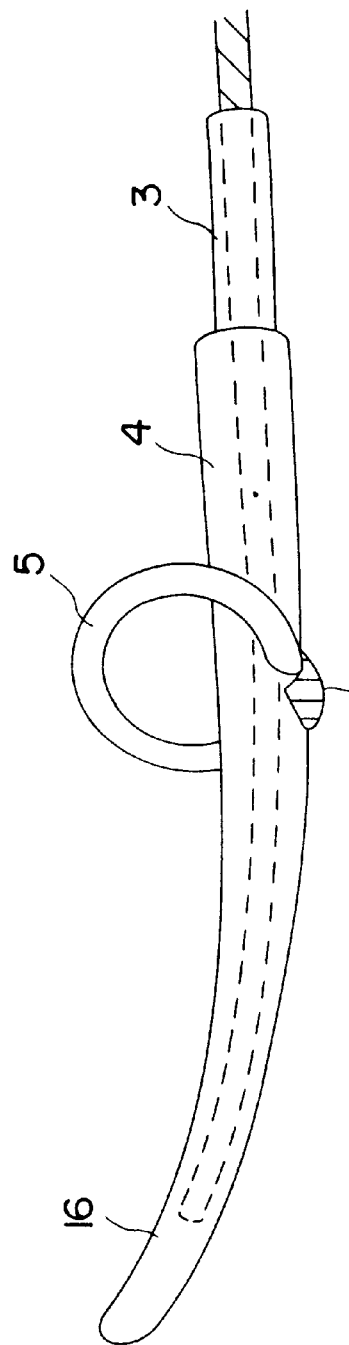
FIG. 5 depicts an alternative embodiment of the present invention.

FIG. 5 depicts an alternative embodiment of the present invention. In this embodiment electrode/anchoring section 4 features a tapered, bent elongated nose 16. Nose is preferably constructed integral with and continuous from electrode/anchoring section. Nose 16 may feature a continuation of the conductor lumen. Nose enhances the steerability and thus ultimate ability of the lead to be properly positioned within the vessel in a manner in which the electrode make the contact with the desired structures of the heart. In particular, the pre shape of the nose determines the ultimate orientation of the lead within the vessel and thus the ultimate orientation of the electrode within the vessel. Selection of a properly shaped nose as well as the orientation of the ring and electrode to the nose thus permits the lead to either communicate with the left atrium, left ventricle or even both left chambers of the heart.

FIG. 6 is an alternative embodiment of the present invention. As seen, in this embodiment the ring 5 features the electrode 10. In this fashion, the ring functions to both wedge the distal end of the lead as well as serve as the platform from which the ring contacts the vessel wall.

FIGS. 7–10 depict alternative embodiments of the present invention in which the relation between the bent elongated nose, ring and electrode are varied. Through these various configurations the different chambers of the heart may be accessed through the coronary sinus or great cardiac vein. FIGS. 7A and 7B depict an alternative embodiment of the present invention specifically intended for electrically accessing the left atrium. FIG. 7A is a perspective view of this embodiment and shows that ring 5 is positioned more towards the distal end of the lead body than is the electrode 10. Moreover, this embodiment additionally features a tapered, bent elongated nose 16. As best appreciated in FIG. 7B, which is a sectional view of the embodiment shown in FIG. 7A taken along the line 7B—7B, ring 5 is disposed at a ninety degree angle relative to nose 16.

Figure 8A:
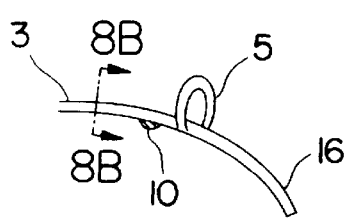
Figure 8B:
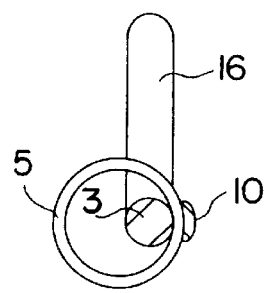

FIGS. 8A and 8B depict an alternative embodiment of the present invention specifically intended for electrically accessing the left ventricle. FIG. 8A is a perspective view of this embodiment and shows that ring 5 is positioned more towards the distal end of the lead body than is the electrode 10. As best appreciated in FIG. 8B, which is a sectional view of the embodiment shown in FIG. 8A taken along the line 8B—8B, ring 5 is disposed at a ninety degree angle relative to nose 16, and on the opposite side as compared to the embodiment shown in FIG. 7A.

Figure 9A:
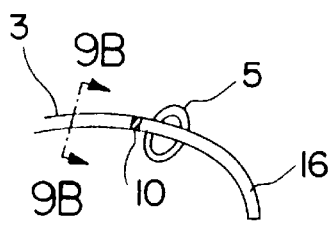
Figure 9B:
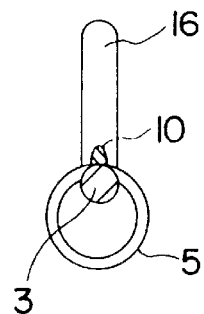

FIGS. 9A and 9B depict an alternative embodiment of the present invention specifically intended for electrically accessing the either the left atrium or left ventricle, depending upon exactly where and how the lead is implanted. FIG. 9A is a perspective view of this embodiment and shows that ring 5 is positioned more towards the distal end of the lead body than is the electrode 10. As best appreciated in FIG. 9B, which is a sectional view of the embodiment shown in FIG. 9A taken along the line 9B–9B, ring 5 is disposed on the opposite side to nose 16.

Figure 10A:
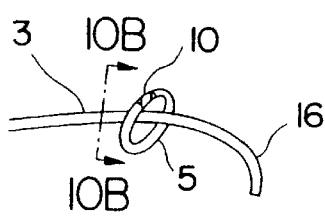
Figure 10B:
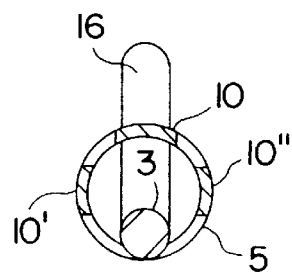

FIGS. 10A and 10B depict an alternative embodiment of the present invention specifically intended for electrically accessing the either the left atrium or left ventricle, depending upon exactly where and how the lead is implanted. FIG. 10A is a perspective view of this embodiment and shows that ring 5 is positioned more towards the distal end of the lead body than is the electrode 10. As best appreciated in FIG. 10B, which is a sectional view of the embodiment shown in FIG. 10A taken along the line 10B—10B, ring 5 is disposed on the same side as nose 16 This embodiment also feature the electrode 10 is positioned on ring 5. As depicted electrode 10 may be positioned on any location about ring, including at position 10, 10' or 10" to illustrate a few possibilities. In this embodiment ring would be fashioned from a polymer having a conductor therein. Conductor would thus couple the electrode to the lead body conductor and thus to the pulse generator.

FIG. 11 depicts an alternative embodiment of the present invention. As seen, in this embodiment lead further features a defibrillation electrode 17 positioned at the distal end. As further seen, lead body 3 has multiple conductors, one coupled to electrode 10 and a second to electrode 17 as is well known in the art. Defibrillation electrode 17 is also constructed in a manner well known in the art. Through this design it is possible, for example, to pace the left atrium and defibrillate the atria(i.e. both the left and right atrium). It would be further possible to pace the left ventricle and defibrillate both ventricles (for example, through the use of an electrode in the inferior vena cava.)

FIG. 12 depicts an alternative embodiment of the present invention. As seen, in this embodiment ring is interrupted and is fashion from a first arc 5–1 and a corresponding opposing second arc 5–2. These arcs cooperate to lodge or wedge lead into position and cause electrode 10 to contact the vessel wall. Each arc, moreover, may be canted or angled relative to lead body as described above and further are similarly dimensioned as ring. In a further embodiment arcs may also incorporate one or more electrodes, represented here as 10', Each of the above described embodiments may further be provided with a surface treatment such as a coating of one or more various compounds or be surface treated to increase biocompatibility. Such coating may include heparin or other anti-thrombus agents, for example, as disclosed in the Cahalan et al. U.S. Pat. No. 5,229,172 assigned to the assignee of the present invention and incorporated herein by reference.

It is to be understood that the present invention is not limited to use only in pacing leads, and may be employed in the construction of many of various type of therapeutic and diagnostic devices, including defibrillation leads, intended to be disposed within the coronary sinus. In fact, for the purposes of this specification and claims, the term "lead" is used herein in its broadest sense and includes any stimulation lead or sensing lead, a combination thereof or any other elongated member, such as a catheter, which may usefully be introduced into a body. For purposes of illustration only, however, the present invention has been described in the context of transvenous pacing lead. In addition, although the term "coronary sinus" has been used, this is for purposes of illustration only and it should be understood the present invention is useful in positioning a lead along any portion of the vascular system, including the great cardiac vein, or any of the other numerous veins or even arteries within the body into which a lead may be implanted.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A medical electrical lead, comprising means for electrically coupling to a pulse generator
    a lead body coupled to the means for electrically coupling, the lead body having a first diameter, a proximal first end, a distal second end, an electrical conductor disposed within the lead body and extending distally from the first end and being electrically connected to the electrical coupling means, and an insulator covering the conductor;
    an electrode/anchoring section positioned near the second end, the electrode/anchoring section having an electrode coupled thereto, the electrode being positioned on a first side of the electrode/anchoring section and being electrically coupled to the electrical conductor; and
    ring means for maintaining the electrode in contact with a blood vessel wall, the ring means defining a flexible loop-shaped member having a first portion thereof attached to the anchoring/electrode section and a second portion thereof extending outwardly away from the first portion and a second side of the anchoring/electrode section, the second side being diametrically opposite from the first side, the ring means having a second diameter greater than the first diameter, the second diameter not exceeding 8 millimeters, the ring means further having a thickness between aoproximately 0.5 mm and 3 mm.

2. A medical electrical lead according to claim 1, wherein the lead body has a center axis, the ring means has a center axis, and the ring means center axis is disposed at an oblique angle with respect to the lead body center axis.

3. A medical electrical lead according to claim 1, wherein the ring means comprises a circular polymeric ring, the ring means being disposed around and tangent to the electrode/anchoring section.

4. A medical electrical lead according to claim 1 wherein the second diameter ranges between approximately 6 mm and 8 mm and the first diameter ranges between approximately 1 mm and 3 mm.

5. A medical electrical lead according to claim 1, wherein the electrode/anchoring section has a distal end, the distal end having a bent nose, the ring means being disposed proximally from the bent nose.

6. A medical electrical lead according to claim 1, wherein the ring is disposed distally from the electrode.

7. A medical electrical lead according to claim 1, wherein the ring means has a width of between approximately 0.5 mm and 4 mm.

8. A medical electrical lead according to claim 1, wherein the ring means comprises a biocompatible material.

9. A medical electrical lead, comprising
    means for electrically coupling to a pulse generator
    a lead body coupled to the means for electrically coupling, the lead body having a first diameter, a proximal first end, a distal second end, an electrical conductor disposed within the lead body and extending distally from the first end and being electrically coupled to the electrical coupling means, and an insulator covering the conductor, the lead body having an electrode disposed near the second end of the conductor, the electrode being positioned on a first side of the lead body and being electrically coupled to the electrical conductor; and
    a pair of flexible arcuately-shaped means for maintaining the electrode in contact with a blood vessel wall, each arcuately-shaped means defining an arcuately-shaped member comprising a first portion attached to the lead body near the second end and a second arcuate portion extending outwardly away from a second side of the lead body, the second side being diametrically opposite from the first side, each arcuate member extending away from the lead a distance defining a second diameter, the second diameter being greater than the first diameter and not exceeding 8 mm.

10. A medical electrical lead according to claim 9, wherein the lead body has a center axis, the arcuately shaped means has a center axis, the arcuately shaped means center axis being disposed at an oblique angle with respect to the lead body center axis.

11. A medical electrical lead according to claim 9, wherein the arcuately shaped means comprises a polymeric material, the arcuately shaped means being disposed around and tangent to the lead body.

12. A medical electrical lead according to claim 9, wherein the arcuately shaped means has thickness of anywhere between approximately 0.5 mm and 3 mm.

13. A medical electrical lead according to claim 9, wherein the second diameter ranges between approximately 6 mm and 8 mm and the first diameter ranges between approximately 1 mm and 3 mm.

14. A medical electrical lead according to claim 9, wherein the lead further comprises an electrode/anchoring section having a distal end, the distal end having a bent nose, the electrode/anchoring section being disposed near the second end, the arcuately shaped means and electrode being attached thereto, the accurately-shaped means being disposed proximally from the bent nose.

15. A medical electrical lead according to claim 9, wherein the arcuately-shaped means are disposed distally from the electrode.

16. A medical electrical lead according to claim 9, wherein the arcuately shaped means has a width of between approximately 0.5 mm and 4 mm.

17. A medical electrical lead according to claim 9, wherein the arcuately shaped means comprises a biocompatible material.

18. A medical electrical lead, comprising
    means for electrically coupling to a pulse generator
    a lead body coupled to the means for electrically coupling, the lead body having a first diameter, a proximal first end, a distal second end, an electrical conductor disposed within the lead body and extending distally from the first end and being coupled to the electrical coupling means, and an insulator covering the conductor, the lead body having first and second sides diametrically opposed to one another;

a loop shaped member for maintaining an electrode in contact with a blood vessel wall, the loop-shaped member having a first portion thereof attached to the lead body near the second end and a second portion thereof extending outwardly away from the second side of the lead body, the second portion including the electrode, the electrode being disposed at an outermost portion thereof and being electrically coupled to the electrical conductor, the loop-shaped member having a second diameter greater than the first diameter, the second diameter not exceeding 8 millimeters, the loop-shaped means further having a thickness between approximately 0.5 mm and 3 mm.

19. A medical electrical lead according to claim 18, wherein the lead body has a center axis, the loop-shaped member has a center axis, and the loop-shaped means center axis is disposed at an oblique angle relative to the lead body center axis.

20. A medical electrical lead according to claim 18, wherein the loop-shaped member comprises a circular polymeric material and is disposed around and tangent to the lead body.

21. A medical electrical lead according to claim 18, wherein the second diameter ranges between approximately 6 mm and 8 mm and the first diameter ranges between approximately 1 mm and 3 mm.

22. A medical electrical lead according to claim 18, wherein the lead body has a distal end having a bent nose and the loop-shaped member is disposed proximally of the bent nose.

23. A medical electrical lead according to claim 1, wherein loop-shaped member has a width of between approximately 0.5 mm and 4 mm.

* * * * *